US012796909B2

(12) United States Patent
Sobol et al.

(10) Patent No.: US 12,796,909 B2
(45) Date of Patent: Nov. 17, 2026

(54) INTERFACE FOR OPTICAL TEST SYSTEM

(71) Applicant: CASE WESTERN RESERVE UNIVERSITY, Cleveland, OH (US)

(72) Inventors: Warren Sobol, Beachwood, OH (US); Alan Dogan, Hillsborough, NJ (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 537 days.

(21) Appl. No.: 18/508,292

(22) Filed: Nov. 14, 2023

(65) Prior Publication Data

US 2024/0156338 A1 May 16, 2024

Related U.S. Application Data

(60) Provisional application No. 63/593,665, filed on Oct. 27, 2023, provisional application No. 63/383,614, filed on Nov. 14, 2022.

(51) Int. Cl.
*A61B 3/00* (2006.01)
*A61B 3/10* (2006.01)

(52) U.S. Cl.
CPC ............ *A61B 3/0083* (2013.01); *A61B 3/102* (2013.01); *A61B 3/0033* (2013.01); *A61B 3/0041* (2013.01)

(58) Field of Classification Search
CPC ... A61B 3/0033; A61B 3/0041; A61B 3/0083; A61B 3/102
See application file for complete search history.

(56) References Cited

PUBLICATIONS

Paul, Samantha, K., et al. Efficient labeling of retinal fundus photographs using deep active learning, Journal of Medical Imaging, Nov./Dec. 2022, vol. 9(6).
Paul, Samantha K., A Systematic Review of Deep Learning Applications for Optical Coherence Tomography in Age-Related Macular Degeneration, Retina, the Journal of Retinal and Vitreous Diseases, 2022, vol. 42, No. 8.
Paul, Samantha, et al., Can the Future be Bright with Advances in Diabetic Eye Care?, Endocrinol Metab Clin N. Am, 2022.
Paul, Samantha, et al. Ellie Zhou, Ankur Mehra, Ian Pan, Warren Sobol; Automatic Identification of Ancillary Features of Diabetic Macular Edema in Optical Coherence Tomography Using Deep Learning. Invest. Ophthalmol. Vis. Sci. 2022;63(7):180—F0027.

*Primary Examiner* — Jack Dinh
(74) *Attorney, Agent, or Firm* — Tarolli, Sundheim, Covell & Tummino LLP

(57) ABSTRACT

An optical test apparatus can be adapted to enable users to self-orient for performing one or more optical tests, including, for example, an optical coherence tomography (OCT) scan. The test apparatus includes a housing, an optical device and an eyecup assembly. The optical device includes an eyepiece. A distal end portion of the eyecup assembly is coupled to the proximal end of the housing so an aperture of the eyecup assembly can align with the optical axis of the eyepiece. The eyecup assembly can be mechanically biased to provide a depth adjustment for at least the proximal end portion of the eyecup assembly relative to the eyepiece in a direction parallel to the optical axis of the eyepiece. The eyecup assembly can be configured as a single-eye design or a dual-eye design.

1 Claim, 9 Drawing Sheets

INTERFACE FOR OPTICAL TEST SYSTEM

CROSS-REFERENCE TO RELATED APPLICATION

This application claims the benefit of priority to U.S. patent application nos. 63/383,614, filed Nov. 14, 2022, and 63/593,665, filed Oct. 27, 2023, each of which is incorporated herein by reference in its entirety.

TECHNICAL FIELD

This disclosure relates to an interface for an optical test system.

BACKGROUND

Various types and configurations of optical test systems are used for performing examinations of an individual's eyes. For many such tests, a technician assists the individual to orient their head relative to the machine for proper alignment of the individual's eye(s) with the optics of the test system. One example of such a system is an optical coherence tomography test unit, which can include a chin rest and head strap.

SUMMARY

This disclosure relates to an interface for an optical test system.

In one example, an optical test system includes a housing having an opening at a proximal end thereof. An optical device resides at least partially within the housing. The optical device has an eyepiece that is aligned with and/or extends through the opening of the housing, and the eyepiece has an optical axis. An eyecup assembly has a sidewall extending between proximal and distal end portions and an aperture extending axially through the sidewall. The distal end portion is coupled to the proximal end of the housing so the aperture is configured to align with the optical axis. The eyecup assembly can be mechanically biased to provide a depth adjustment for at least the proximal end portion of the eyecup assembly relative to the eyepiece in a direction parallel to the optical axis thereof.

In another example, an optical coherence tomography (OCT) test system includes a housing that contains an OCT device having an eyepiece having an optical axis. An eyecup assembly is coupled to the housing and configured to place one or more respective eyes of a user at an expected position and orientation relative to the eyepiece to enable the user to implement a self-acquired scan. The eyecup assembly has a sidewall extending between proximal and distal end portions and an aperture extending axially through the sidewall, and the distal end portion is coupled to a proximal end of the housing so the aperture is arranged to align with the optical axis. The eyecup assembly is mechanically biased to provide a depth adjustment for at least the proximal end portion of the eyecup assembly relative to the eyepiece in a direction parallel to the optical axis thereof. A control device is configured to control the OCT device in response to a user input, in which the user input is provided in response to at least one of (1) activation of a switch or (2) activation of a graphical user interface element.

DETAILED DESCRIPTION

Figure 1:
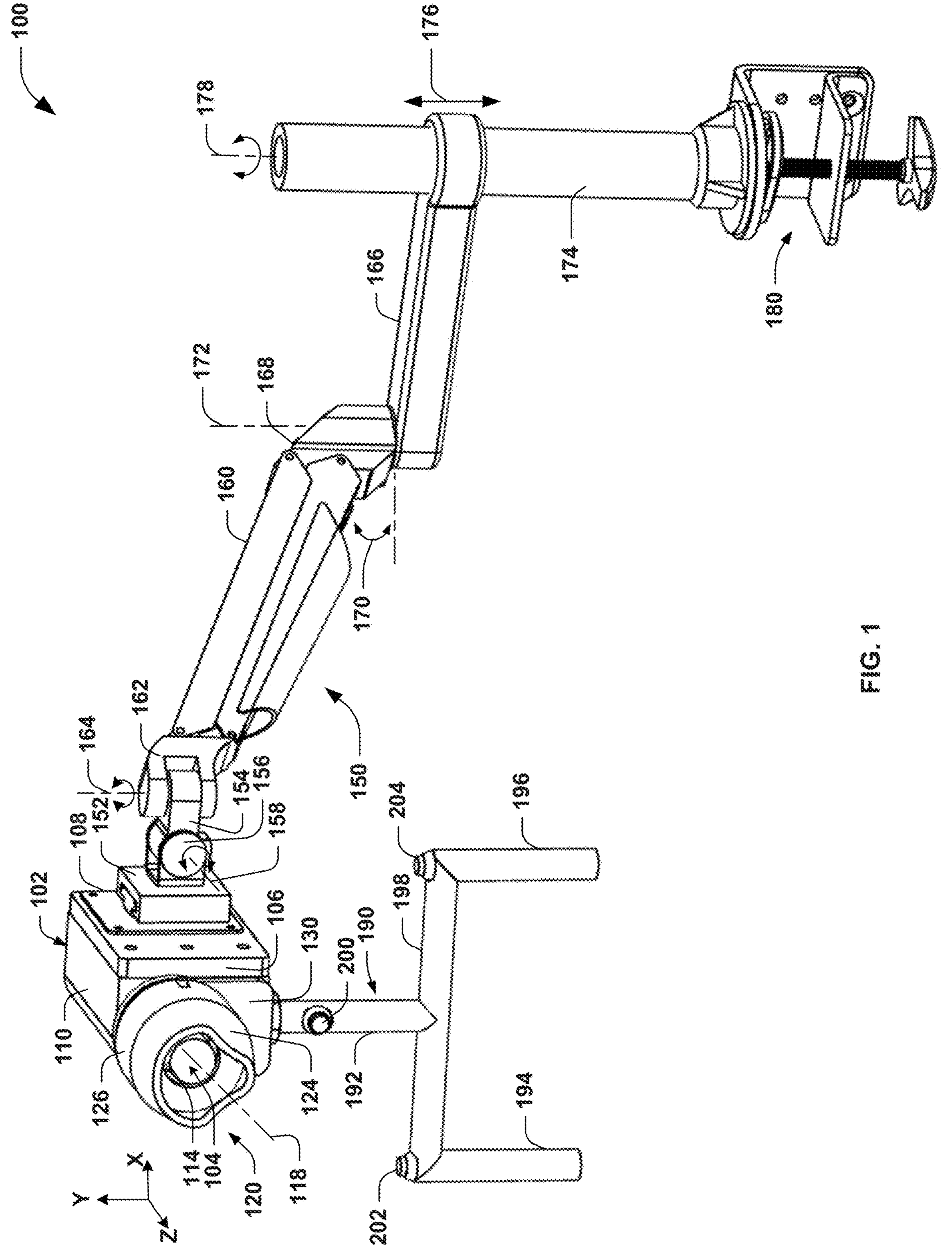
FIG. 1 is an isometric view of an example of an optical test apparatus.

This disclosure relates to an interface for an optical test system. The interface is adapted to enable users to self-orient for performing one or more optical tests, such as an optical coherence tomography (OCT) or other optical scan.

As an example, the test apparatus includes a housing having an opening at a proximal end of the housing and an optical device at least partially within the housing. The optical device includes an eyepiece having an optical axis. The eyepiece can be aligned with and/or extend through the opening of the housing. An eyecup assembly has a sidewall extending between proximal and distal end portions and an aperture extending axially through the sidewall. The eyecup assembly can be configured as a single-eye design or a dual-eye design. The distal end portion is coupled to the proximal end of the housing so the aperture of the eyecup assembly can align with the optical axis of the eyepiece. The eyecup assembly can be mechanically biased to provide a depth adjustment for at least the proximal end portion of the eyecup assembly relative to the eyepiece in a direction parallel to the optical axis of the eyepiece.

In a further example, the single-eye design includes a proximal end portion configured to contact on or around an orbit of a respective eye such that the eyepiece will partially or completely block out ambient light from the optical path. The distal end portion of the single-eye design is fixed with respect to the proximal end of the housing. Thus, a user position each of the user's eyes individually with respect to the eyecup for performing the optical test (e.g., OCT scans).

The dual-eye design includes a proximal end portion of the eyecup assembly having a proximal edge adapted to fit against a user's face, with a foam interface to conform to general bony orbital structures surrounding an ocular region of the user's face (e.g., around both eyes). In some examples, such as where the optical device includes a single eyepiece, the eyecup assembly is configured to move relative to the housing in a direction orthogonal to the optical axis to move the eyecup assembly between first and second test positions. Thus, a user can activate the optical device to obtain test data for one eye when the eyecup assembly is in the first test position and, after moving the eyecup assembly to the second test position, activate the optical device to obtain test data for the other eye. The optical test system described herein further enables tests to be performed by the user in the absence of intervention by a health care provider or technician.

FIGS. 1-4 depict an example of an optical test apparatus 100 that can be used to implement one or more optical tests.

The test apparatus 100 includes a housing 102 that contains an optical device 104. The optical device 104 includes eye examination equipment (e.g., optical components, an imaging device, hardware and software) configured to measure optical properties of a patient's eye, such as in a non-invasive manner. For example, the optical device 104 includes an OCT device configured to scan a laser across a user's eye (or eyes) to generate an OCT image (e.g., a two-dimensional or three-dimensional image) of the eye. Some useful examples of OCT devices that can be used to implement the optical device 104 are disclosed in U.S. Pat. No. 10,156,434. In another example, different types of OCT devices can be used. Additionally or alternatively, the optical device 104 can include one or more other type of eye measurement device, such as including a non-mydriatic fundus camera, a keratometer, auto refractor, or a tonometer to name a few. It is thus to be appreciated that the test apparatus 100 can be adapted to perform one or more types of measurements of or relating to an individual's eye.

Figure 2:
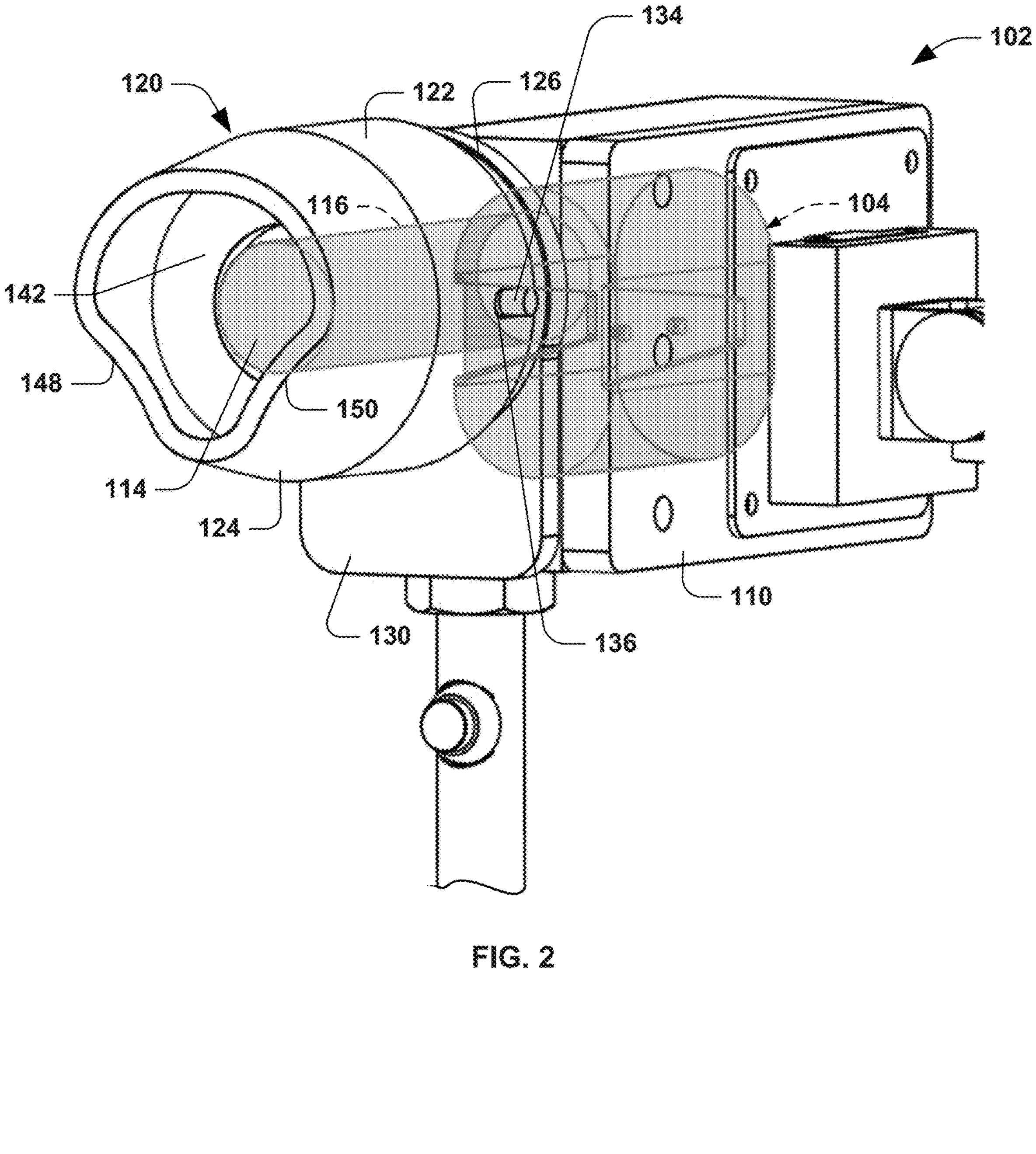
FIG. 2 is an enlarged view of part of the test apparatus of FIG. 1.
Figure 3:
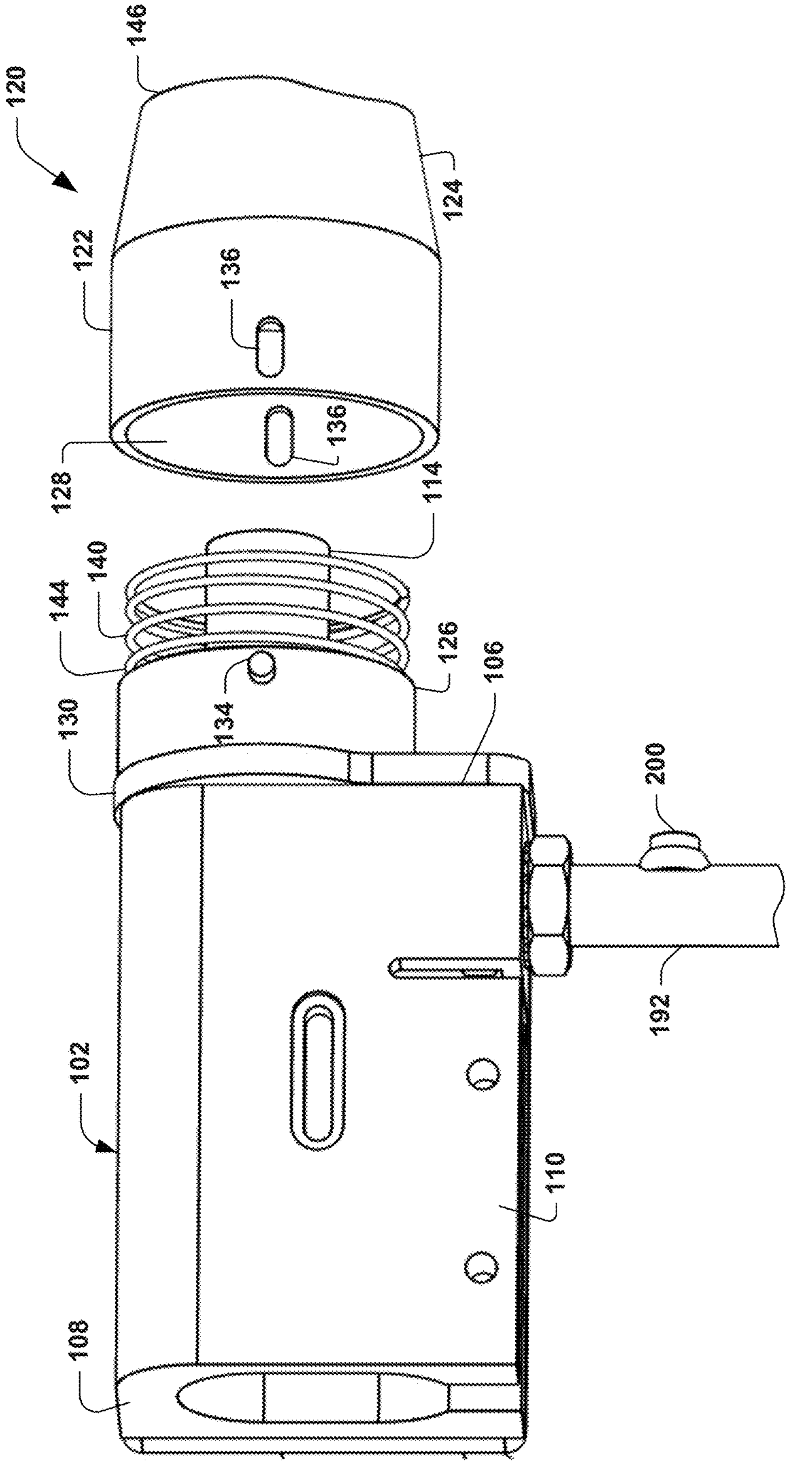
FIG. 3 is an enlarged view of part of the test apparatus of FIG. 1 showing an end portion in an exploded view.

The housing 102 has proximal and distal end portions 106 and 108, and a sidewall portion 110 extending between the proximal and distal end portions 106 and 108. The housing 102 also includes an opening 112 extending through the proximal end portion 106 of the housing. The housing 102 can be a rigid material, such as a metal, a plastic material, or a combination of metal and plastic materials suitable for enclosing the optical device 104. As shown in FIGS. 2 and 3, the optical device 104 can be partially located within the housing 102. For example, the optical device 104 includes an eyepiece 114, such as configured as cylindrical barrel 116, which is aligned with and/or extends through the opening 112 of the housing 102. The eyepiece 114 also has an optical axis, shown at 118, such as extending along a centerline of the barrel 116.

The optical test apparatus 100 also includes an eyecup assembly 120 having a sidewall 122 extending between proximal and distal end portions 124 and 126. The sidewall 122 has an interior wall that defines an aperture 128 extending axially through the eyecup assembly 120. The proximal and distal end portions 124 and 126 can be separate portions that are coupled together. For example, as shown in the exploded view of FIGS. 3 and 4, the distal end portion 126 of the assembly 120 is coupled to a mounting plate 130 at the proximal end 106 of the housing 102. The mounting plate 130 includes an aperture 132 arranged and configured to receive a portion of the eyepiece barrel 116 that extends into the aperture 128 of the eyecup assembly. The apertures 128 and 132 thus are aligned with the optical axis 118, such that light from the optical device 104 can transmit through the eyecup assembly 120 for performing scans or other optical measurements (e.g., depending on the type of optical device) of a user's eye positioned at a proximal edge 134 of the eyecup assembly.

The proximal end portion 124 of the eyecup assembly 120 can be arranged and configured to be axially movable in a direction parallel to the optical axis 118 to provide a depth adjustment for the eyecup relative to the eyepiece 114. For example, proximal end portion 124 is configured to receive a proximal part of the distal end portion 126 with a distal interior sidewall to limit the extent of the axial movement of the proximal end portion relative to the distal end portion 126. The distal end portion can include one or more detents 134 extending outwardly from a surface thereof. The proximal end portion can include slots 136 arranged and configured to receive the detents 134 therein when assembled, such as shown in FIGS. 1 and 2. Other mechanisms can be used to provide for the depth adjustment.

As a further example, the eyecup assembly 120 includes a biasing element 140 between the proximal and distal end portions 124 and 126 to mechanically bias (e.g., mechanically dampen) the depth adjustment. For example, each of the proximal and distal end portions includes a respective flange (e.g., a collar or rim) 142 and 144 having opposing surfaces, and the biasing element 140 is positioned between the respective flanges to apply force to urge the proximal and distal end portions 124 and 126 axially apart from each other. Because the distal end portion 126 and eyepiece 114 both have fixed positions relative to the housing 102, the proximal end portion 124 of the eyecup assembly 120 can be moved by applying force on a proximal edge 146 thereof (e.g., when a user presses or pushes the proximal end portion 124 towards the housing 102). The biasing element 140 can be implemented as a spring (as shown), deformable polymer (e.g., an elastically deformable foam) or other structure adapted to mechanically bias the depth adjustment of the proximal end portion 124 or the eyecup assembly altogether.

Figure 4:
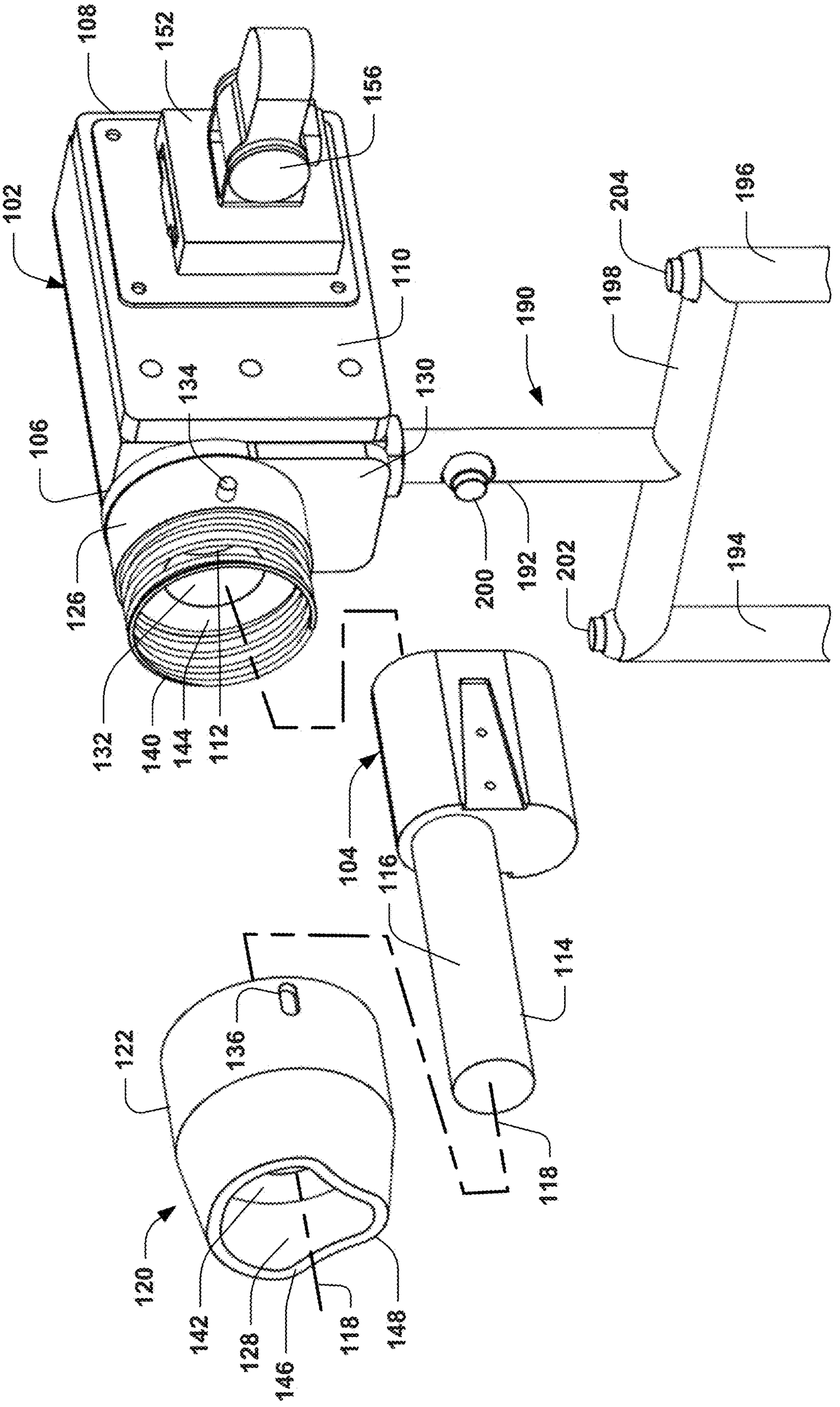
FIG. 4 is an enlarged partially exploded view of part of the test apparatus of FIG. 1.

As shown in FIGS. 2 and 4, the proximal edge 146 of the eyecup assembly is arranged and configured to fit (e.g., snuggly) against a user's face surrounding an orbit of a user's respective eye. The proximal edge 146 is curved radially inwardly at lower sections 148 and 150. The inwardly curved sections 148 and 150 are configured to fit around a user's nose when fitted against the user's face for testing the right as well as the left eye. The proximal end portion 124 of the eyecup assembly is further configured to place the respective eye, during fitting, at an expected or predictable position (e.g., a distance along the optical axis 118) and orientation relative to the eyepiece 114 of the optical device.

As shown in FIG. 1, the optical test apparatus 100 can also include a mounting apparatus 150 coupled to the housing 102 and configured to support the housing relative to a surface. The structure to which the mounting apparatus coupled can depend on the use environment. The mounting apparatus 150 can be adjustable in multiple degrees of freedom (e.g., two or more degrees of freedom) to enable positioning of the housing 102 and eyecup assembly 120. In the example of FIG. 1, the mounting apparatus 150 is adapted to enable a user to adjust the position of the test apparatus in up to five or six degrees of freedom, such as along X, Y, and Z directions as well as roll, pitch and yaw. The adjustability is a result of an arrangement of arms and other support structures coupled to each other through various articulated or other joints.

In the example of FIG. 1, the mounting apparatus 150 includes a mounting bracket 152 coupled to the housing 102. The coupling between the bracket 152 and housing 102 can be fixed or removable, such as to enable the housing to be removed and replaced from the mounting apparatus 150. A proximal end of a first arm 154 is coupled to the bracket 152 through a hinge joint 156. The hinge joint 156 permits rotation of the housing 102 about an axis 158 extending through the joint 156. A distal end of the arm 154 is coupled to a proximal end of a second arm 160 through another hinge joint 162. The hinge joint permits rotation of the housing 102 and arm 154 about an axis 164 extending through the joint 162, which is orthogonal to the axis 158. For example, the axis 158 extends in the Z direction and the axis 164 extends in the Y direction. The arm 160 is coupled to another arm 166 through another joint 168 to enable adjustment along multiple degrees of freedom. For example, the joint 168 permits movement of the arm 160 over a range of angles 170 with respect to the support arm 166. The joint 168 can also be configured to rotate the arm 160 (along with proximal parts of test apparatus about an axis 172. The support arm 166 can be slidably coupled to an elongated arm 174 to enable movement of arm 166 in an axial direction 176 along the arm 174 between proximal and distal ends of the arm 174. The coupling between the arms 166 and 174 can also permit rotation of the arm 166 about a longitudinal axis 178 of the arm 174.

The mounting apparatus 150 also includes a mounting bracket 180 at a distal end of the arm 174. The mounting bracket 180 can include one or more attachment features adapted to couple the mounting apparatus 150 to a variety of structures, such as a table top, desk, wall, pole, ceiling, pivoting table top, and the like. For example, the mounting bracket 180 can include a clamp, a plate with through holes (e.g., for bolting or screwing into a surface) or other mounting feature to fix the mounting apparatus at a desired location.

Additionally, the optical test apparatus 100 can include a handle 190 coupled to and extending from the housing 102. For example, the handle can be coupled to a side (e.g., bottom side of the housing by a fastener (e.g., threaded fastener, rivet, weld, etc.). The handle 190 can be grasped by one or more hands of a user, and used to adjust the eyecup assembly to a desired position and orientation for the user. In the example of FIG. 1, the handle 190 includes a connecting arm 192 having one end coupled to the housing 102 and another end coupled to an inverted U-shaped handle that includes spaced apart bars having respective gripping portions 194 and 196 extending from crossbar 198. The connecting arm 192 can be coupled to a medial location along the cross bar. The connecting arm 192 and gripping portions 194 and 196 can extend parallel to each other along the Y-direction on opposite sides of the housing 102. The gripping portions 194 and 196 can include hand grips (now shown) or coating of a pliant material, such as a natural or synthetic rubber material. Other handle configurations also can be used in other examples.

In some examples, the optical test apparatus 100 can include one or more buttons. In the example shown in FIG. 1, the test apparatus 100 includes an arrangement of buttons 200, 202 and 204 located on the handle 190. Each of the buttons 200, 202 and 204 is configured to provide a control signal in response to activation of the respective button. The buttons 200, 202 and 204 can be configured to provide the same control signal for performing a particular control function. Alternatively, the buttons 200, 202 and 204 can be configured to provide unique control signals for performing distinct functions. The buttons 200, 202 and 204 can be coupled to a control system (e.g., a control device and/or computing apparatus—see, e.g., FIG. 9) that is configured to control the optical device 104. In some examples, the control system can be configured to light the buttons 200, 202 and 204 (e.g., via an LED) to help guide the user during testing. For instance, the buttons can be illuminated green or white when ready for testing and red or off (no illumination) to indicate testing is complete or the apparatus is not ready.

The control system can be implemented within the housing 102, such part of the optical device 104 or a separate unit, or the control system can be external to the housing 102, such as coupled to the optical device through a link (e.g., a physical or wireless link). The control system is thus configured to control the optical device 104 to perform an optical test and provide test data in response to one or more control signal(s). Alternatively or additionally, another device (e.g., a mobile device, such as a cellular telephone or tablet computer, notebook computer, specially configured interface device, etc.) can be configured to provide a control signal to activate a respective test function. As a further example, where the optical device is an OCT device, the OCT device is configured to perform a number of one or more scans and provide respective test data, which is representative of a volume scan based on the images acquired during each scan. The scan(s) can be initiated responsive to activation of one or more switches, such as shown as buttons 200, 202, 204. Other types of mechanical and/or electromechanical switches can be used in other examples, such as described herein. Each scan can include a plurality of image frames, such as a video segment acquired over an acquisition time period (e.g., a number of seconds). The number of image frames for a given scan can be programmable or fixed for a given application, such as 100, 128, 256, 512 or another desired number of frames.

As a further example, a control system (e.g., control device and/or computing device) includes executable instructions programmed to evaluate the scans for quality. The evaluation can include a process that involves techniques, such as thresholding, contour line mapping, convolution-based analysis or similar image processing function. Additionally or alternatively, other methods, such as using a machine learning classifier, feature extraction or the like can be used to ascertain an indication of the quality of the scans and/or each image frame thereof. The control system thus can determine if a majority of scans from the volume are diagnostically sufficient or diagnostically insufficient quality, such as based on preset thresholding. If a scan volume is determined to be diagnostically insufficient, guidance can be provided to instruct the user to retake the scan. The system can be configured to permit the scan to be retaken up to a predetermined number (e.g., 3, 4 or another number) of times. After the predetermined number of scan attempts, the control system can instruct the patient (e.g., via visual and/or audible feedback) to reorient themselves with respect to the eyecup assembly and reactivate the scan. If a scan is determined to be diagnostically sufficient, feedback can also be provided to the user (e.g., via visual and/or audible feedback) to indicate the scan is complete. For example, visual feedback can be on a display or LED that is visible within the eyecup assembly and/or on a separate display device (e.g., coupled to or part of the optical unit). Also, or alternatively, the feedback can include real-time feedback (e.g., audible and/or visual feedback) to indicate the quality of image scans being acquired during testing. Such real-time feedback can help instruct the user properly orient their head relative to the eyepiece.

Figure 5:
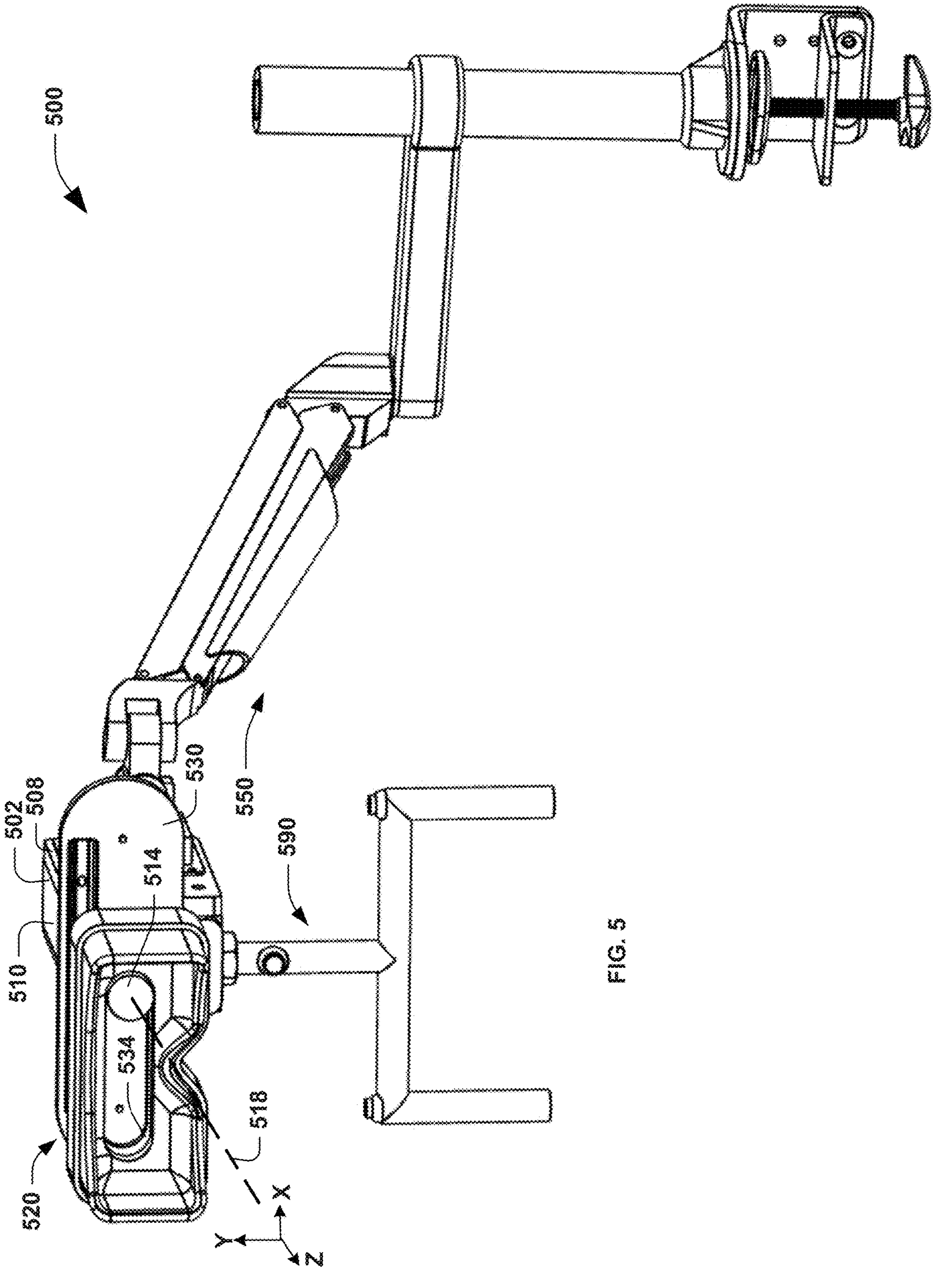
FIG. 5 is an isometric view of another example of an optical test apparatus.

FIGS. 5-8 show an example of another optical test apparatus 500 that can be used to implement one or more optical tests. The test apparatus 500 has a similar configuration to the example of FIGS. 1-4. The test apparatus 500 includes a housing 502 that contains an optical device 504. The housing 502 and optical device 504 can have the same configuration as the housing 102 and optical device 104 described herein; although different configurations could also be used. Briefly, the housing 502 has proximal and distal end portions 506 and 508, and a sidewall portion 510 extending between the proximal and distal end portions 506 and 508. The housing 502 also includes an opening 512 extending through the proximal end portion 506 of the housing. The optical device 504 includes an eyepiece 514, such as having a cylindrical barrel 516 that is aligned with and/or extends through the opening 512 of the housing 502. The eyepiece 514 also has an optical axis, shown at 518. In the example of FIG. 5, the optical axis extends parallel to a Z-direction of a three-dimensional coordinate system having orthogonal axes X, Y and Z. The optical device 504 includes eye examination equipment (e.g., optical components, imaging device, hardware and software) configured to measure optical properties of a patient's eye, such as in a non-invasive manner. For example, the optical device 504 is an OCT device, such as described herein.

The optical test apparatus 500 also includes an eyecup assembly 520. In the example of FIGS. 5-8, the eyecup assembly 520 has a dual-eye configuration. For example, the eyecup assembly 520 is in the form of goggles or a mask having a proximal edge 522 arranged and configured to fit against a user's face surrounding an ocular region of the user's face. A rubber or foam layer can be applied at the proximal edge 522 to increase conformability to the user's face. The dual-eye configuration of the eyecup assembly 502 enables a user to place the eyecup assembly in the same position against the user's face for performing optical tests on both the left and right eyes.

The eyecup assembly 520 includes proximal and distal end portions 524 and 526, and a sidewall 528 portion extending between the proximal and distal end portions 524 and 526. The distal end portion 526 is coupled to the proximal end 506 of the housing 502.

Figure 7:
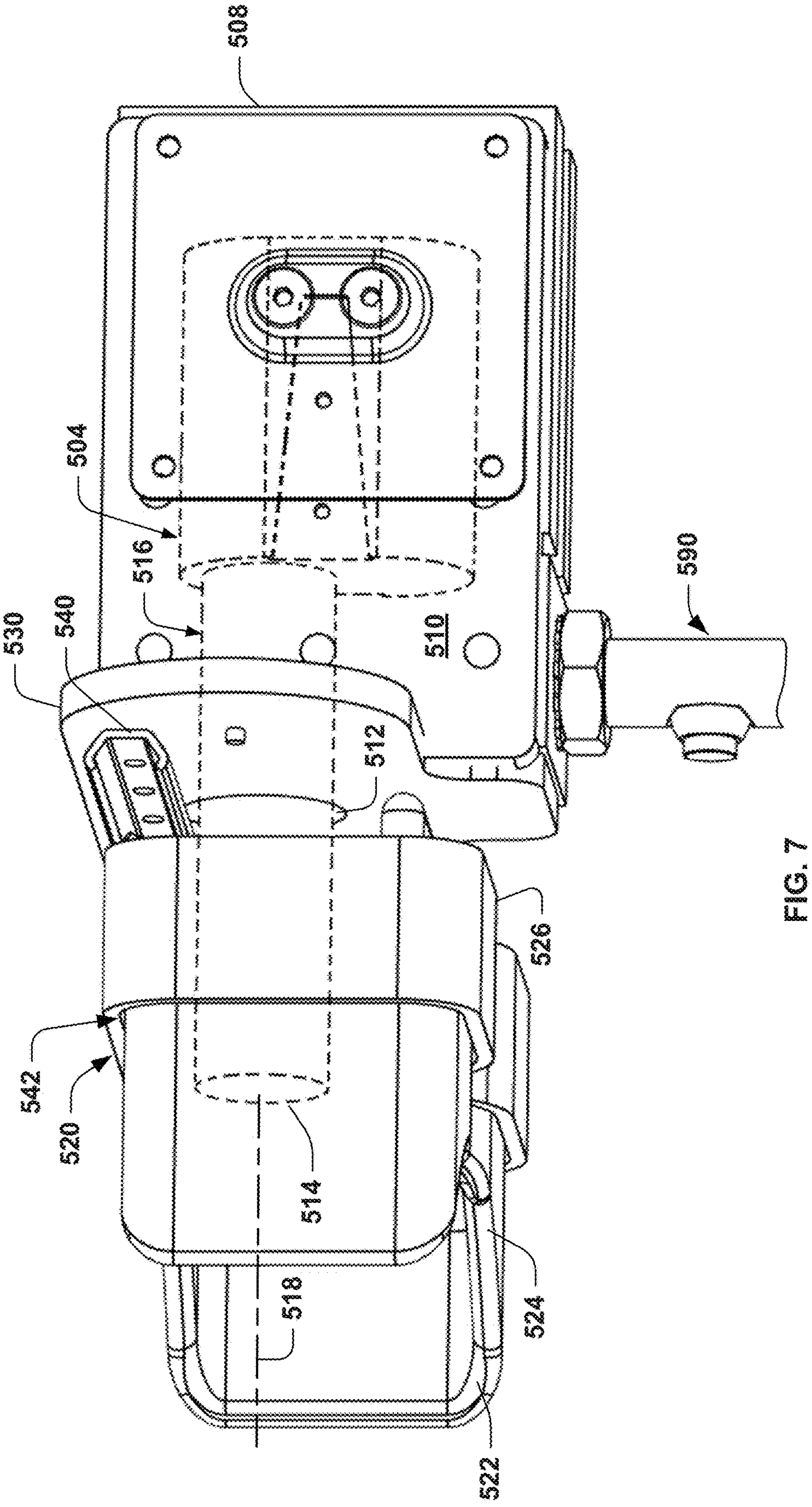
FIG. 7 is an enlarged view of part of the test apparatus of FIG. 4 in which portions are hidden to shown internal parts of a housing.

In some examples, the test apparatus 500 includes a mounting plate 530 at the proximal end 506 of the housing 502. The mounting plate 530 includes an aperture 532 that is aligned with the housing aperture 512 and is configured to receive a portion of the eyepiece barrel 516, such as shown in FIG. 7. The eyecup assembly 520 also includes an aperture 534 extending in a viewing direction to provide a line of sight through the eyecup aperture to the eyepiece 514 and, in some examples, a portion of the eyepiece barrel 516 extends from the housing into an interior of the eyecup assembly 520 to terminate in a proximal end of the eyepiece. The apertures 528, 532 and 534 thus are aligned with the optical axis 518, such that light going to and from the optical device 504 can transmit through the eyecup assembly 520 for performing scans or other optical measurements (e.g., depending on the type of optical device) of a user's eye positioned at a proximal edge 522 of the eyecup assembly. The proximal end portion 524 of the eyecup assembly can further configured to place the user's eyes at an expected or predictable position (e.g., a distance along the optical axis 518) relative to the eyepiece 514 of the optical device to enable optical testing of one or more eyes.

Figure 8:
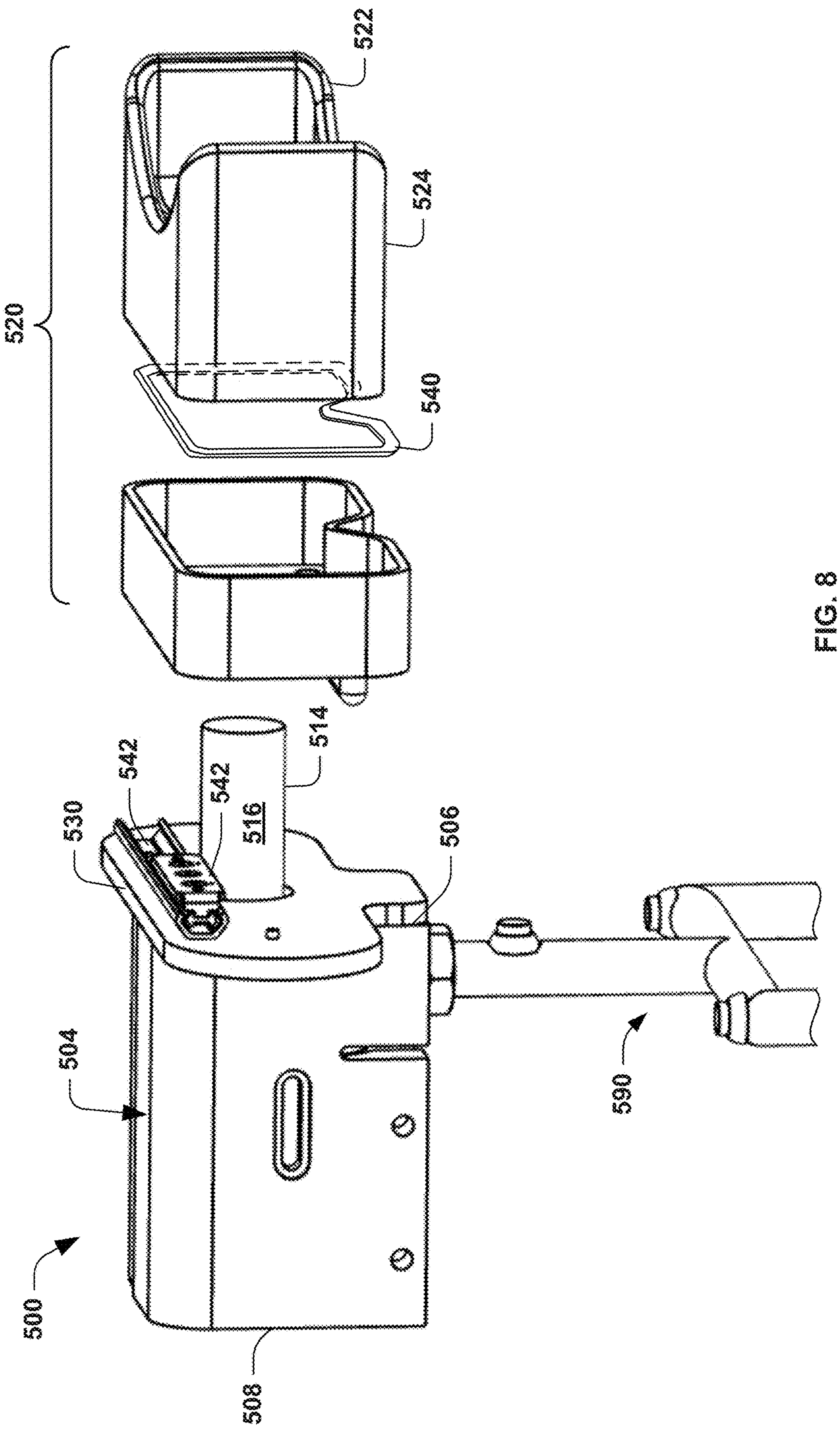
FIG. 8 is enlarged partially exploded view of part of the test apparatus of FIG. 4.

The proximal and distal end portions 524 and 526 can be separate portions that are coupled together, such as shown in the exploded view of FIG. 8. For example, the distal end portion 526 includes a receptacle configured to receive a distal end part of the proximal assembly portion 524 therein. Alternatively, the distal end portion 526 could be received in a corresponding receptacle at the distal end of the proximal end portion 524. In an example, the proximal end portion 524 of the eyecup assembly 520 can be arranged and configured to be axially movable relative to the distal end portion 526 in a direction parallel to the optical axis 518 to provide for depth adjustment for the eyecup assembly relative to the eyepiece 514.

As a further example, as shown in FIG. 8, the eyecup assembly 520 includes a biasing element 540 between the proximal and distal end portions 524 and 526 to mechanically bias (e.g., mechanically dampen) and provide depth adjustment. For example, each of the proximal and distal end portions 524 and 526 includes a respective flange (e.g., a collar or rim—not shown) having opposing surfaces, and the biasing element 540 is sandwiched between the respective flanges to apply force to urge the proximal and distal end portions 524 and 526 axially apart from each other. The biasing element 540 can be implemented as a deformable foam (as shown), a spring, or other structure adapted to mechanically bias the depth adjustment of the proximal end portion 524 or the eyecup assembly altogether. In examples where the distal end portion 526 and eyepiece 514 both have fixed positions relative to the housing 502, the proximal end portion 524 of the eyecup assembly 520 can be moved by applying force on a proximal edge 522 thereof (e.g., when a user presses or pushes the proximal end portion 524 towards the housing 502).

For the dual eye configuration having a single eyepiece, the eyecup assembly 520 can be configured to move relative to the housing 502 in a direction orthogonal to the optical axis 518 (e.g., in the X-direction) to move the eyecup assembly between first and second test positions. To enable movement of the eyecup assembly between respective test positions, the aperture 534 can be arranged configured as an elongated slot in a distal wall of the proximal and/or distal end portions 524 and 526. The slot has a width configured to receive a proximal end portion the eyepiece therein and long diameters during the movement of the eyecup assembly between the first and second test positions, such as described herein. In other examples, separate eyepieces could be provided for each eye location to obviate the need for laterally moving the eyecup assembly; though at an additional expense.

Figure 6:
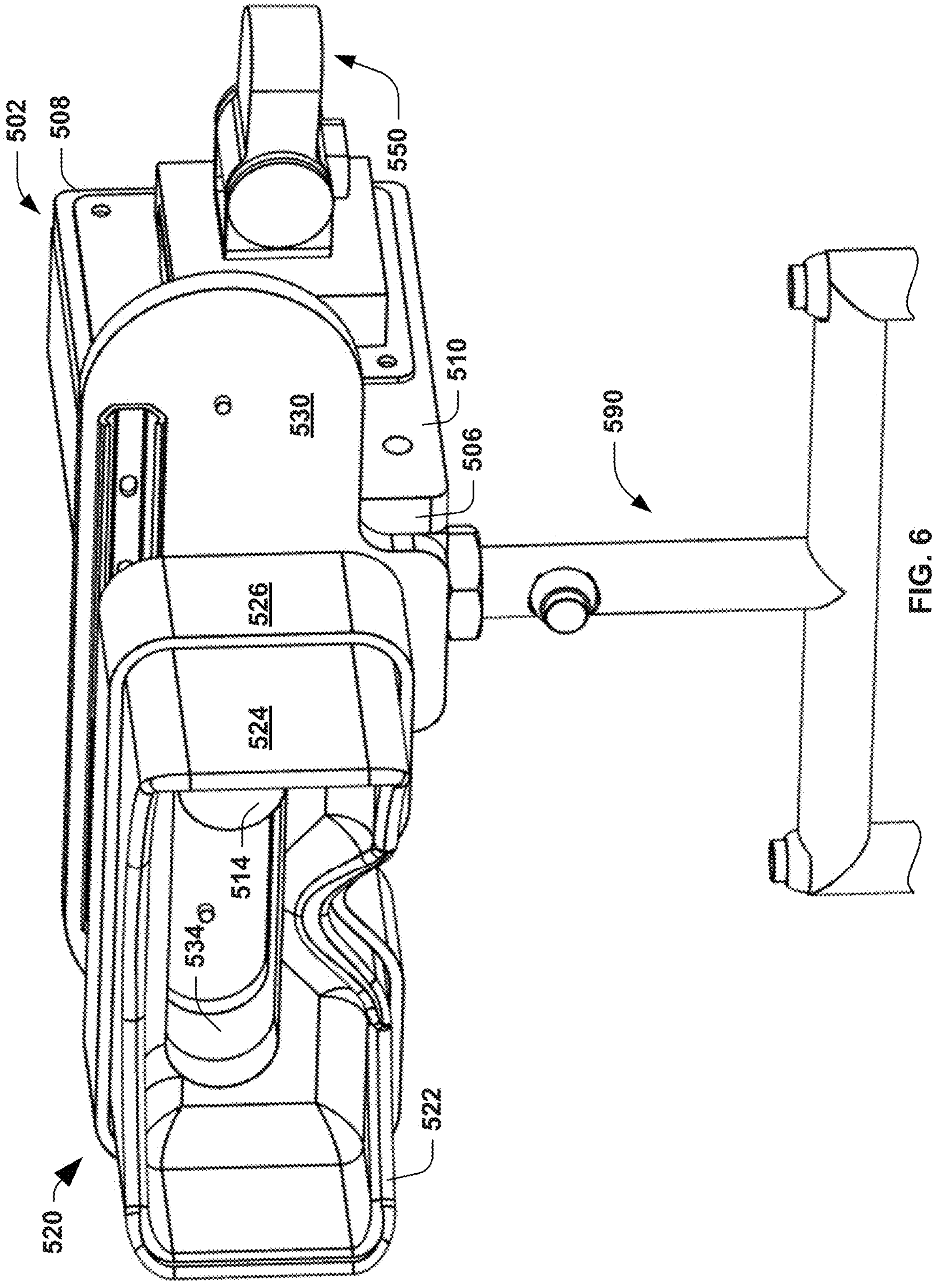
FIG. 6 is an enlarged view of part of the test apparatus of FIG. 4.

As an example, a track (e.g., a linear length of a rail) 540 is coupled at the proximal end 506 of the housing 502, such as attached to the mounting plate 530. A slide 542 can be coupled (e.g., by fasteners) to a distal surface of the distal end portion 5026 of the eyecup assembly 520. The slide 542 is adapted to be coupled to the track 540 to enable lateral movement of the slide along the track between spaced apart edges of the track 540. The track 540 can include stops at opposing ends of the track to define first and second test positions. The stops can be spaced apart from each other along the track a distance that approximates a typical pupillary distance. For example, at the first test position, such as shown in FIGS. 5 and 6, the eyecup assembly 520 is positioned to align a user's right eye with the optical axis 518 of the eyepiece for testing the right eye. The eyecup assembly 520 can be moved laterally to the second test position (not shown) to align a user's left eye with the optical axis 518 of the eyepiece for testing the left eye. A catch or locking mechanism can be provided to hold the eyecup assembly at the desired test positions.

The optical test apparatus 500 can also include a mounting apparatus 550, which can be coupled to the housing 502 to provide multiple degrees of freedom for moving the test device in three-dimensional space. The mounting apparatus 550 can be mounted to a surface (e.g., desk, wall, table, etc.). The mounting apparatus 550 can be the same as shown and described with respect to FIGS. 1-4. Different types of mounting apparatuses can be used in other examples.

Additionally, the optical test apparatus 500 can include a handle 590 coupled to and extending from the housing 502. The handle 590 provides an ergonomic way to enable a user to adjust the position and orientation of the optical test apparatus. The handle 590 can be the same as the handle 190 of FIGS. 1-4, including an arrangement of buttons (e.g., buttons 200, 202, 204) for a user interact with and control the optical device 504 as described herein.

Figure 9:
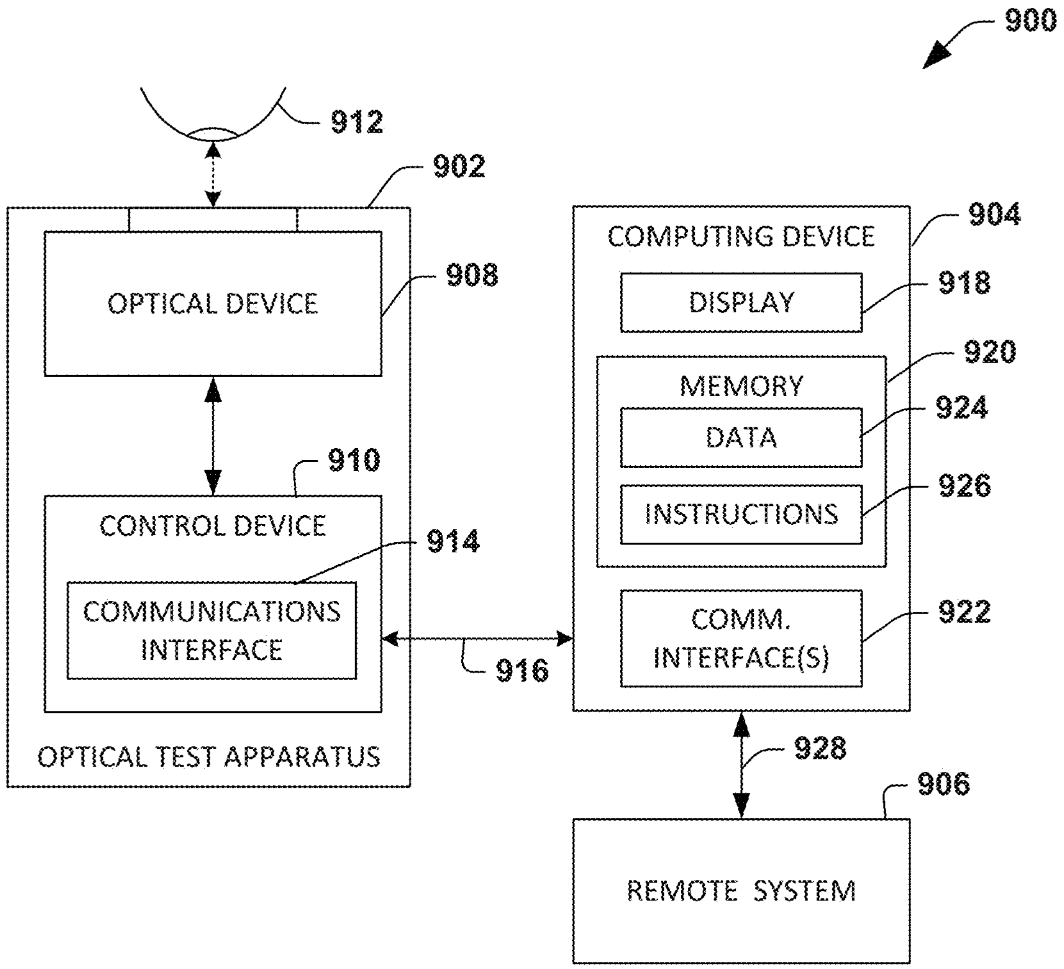
FIG. 9 is a block diagram of an example optical test system.

FIG. 9 is a block diagram of an example optical test system 900. The system 900 includes an optical test apparatus 902, a computing device 904 and a remote system 906. The optical test apparatus 902 such as can be implemented by test apparatuses 100 and 500, described herein. As shown in FIG. 9, the optical test apparatus 902 includes an optical device 908 and a control device 910. The examples of FIGS. 1-8 depict useful examples of test apparatuses 100 and 500 that can be used to implement the optical test apparatus 902. In much of the following description, the computing device 904 is referred to as a computing device; however, the computing device can be implemented in other forms, such as part of a stand-alone desktop computing device or as specialty purpose computer. For example, the computing device 904 can be integrated with the control device 910 and/or the optical device 908.

As described herein, the optical device 908 can be an OCT device that includes an OCT spectrometer and associated electronics configured to control an OCT scanner having optical components (e.g., lenses and tubes, grating, mounts and mirrors) arranged and configured to scan one or more patient's eyes, schematically shown at 912, and acquire OCT images of the eye. The optical device 908 is another example of (or part of) the optical devices 104 and 504 described herein. The above-incorporated U.S. Patent Pub. No 2021/0378505 discloses examples of OCT devices that can be used to implement the optical device 908, 104 and 504 herein. Other OCT devices can be used in other examples, including OCT hardware systems available from Lumedica Systems Inc. as well as other vendors.

In the example of FIG. 9, the optical device 908 is coupled to the control device 910 through a link. The control device 910 can be a computing apparatus programmed to control the optical device 908 and to control communication of instructions and data to and from the optical test apparatus 902. The control device 910 includes electronics (e.g., hardware and software), including a communications interface 914. For example, the communications interface 914 is implemented as a communications network device configured to communicate data through a wireless communications link, such as a Wi-Fi, Bluetooth or a cellular data link. As a further example, the communications interface 914 is configured to implement a wireless network to enable a secure connection over a wireless link 916 between the control device 910 and the computing device 904. The communications interface 914 can implement a peer-to-peer or another connection (e.g., infrastructure-based connection) configured to use security protocols for setup of and access to the communications link 916. In further examples, the communications interface 914 is configured to communicate using a network communication over a physical link 916 between the control device 910 and the computing device 904.

The control device 910 is programmed to control the optical device 908 to store test data in memory, such as may be part of the optical device 908 and/or the control device 910. In an example, the optical device 908 is an OCT device and the control device 910 is programmed to control the OCT device record OCT images and store the OCT images as OCT image data in the memory, such as responsive to a user input (e.g., activation of a switch or graphical user interface element).

As an example, the computing device 904 includes a display 918, non-transitory memory 920 and one or more communications interfaces 922. In some examples, the computing device 904 is a mobile device, such as a smartphone, a tablet or laptop computer, which may belong to the user or be mounted to a table or other structure where the optical device 908 is mounted (e.g., in a common housing or as a separate structure coupled to the optical device 908). In an example, the display 918 is implemented as a touch screen interface, which the patient or other user can use to input instructions or commands for controlling the optical device 908 and the computing device 904, as disclosed herein. The computing device 904 can include another user interface (e.g., keypad and/or other buttons or switches) that can be used to input instructions and commands. In some examples, the computing device 904 is programmed to provide a screen interface or smart phone integration with a tutorial to provide instructions to the user for operating the optical test apparatus 902.

The computing device 904 can be a smart phone or another device, such as a tablet or laptop computer, which may belong to the user or mounted to a table or other structure where the optical test apparatus 902 is located (e.g., mounted to a surface). In other examples, the computing device 904 can be coupled to or integrated into the optical system 902. In an example, the display 918 is implemented as (or includes) a touch screen interface, which the patient or other user can use to input instructions or commands for controlling the optical device 908 and the computing device 904. The non-transitory memory 918 is configured to store data 924 and instructions 926, and a processor (not shown) is configured to access the memory and execute the instructions stored in the memory. In another example, a touch screen interface of the computing device 904 can be mounted to or in (partially or wholly) the housing that contains the control device 910, which is coupled to the optical device 908. In a further example, the housing of the apparatus 902 can contain two or more (e.g., all) of the optical device 908, the control device 910 and the computing device 904.

As mentioned, the computing device 904 also includes one or more communications interfaces 922, each configured to communicate over a respective network. For example, the instructions 926 are configured to establish a communications link 916 between a respective communications interface 922 of the computing device 904 and the communications interface 914 of the optical test apparatus 902. This can be done using the native operating system and controls of the computing device 904. The interfaces 914 and/or 920 can be configured to implement the link 928 according to a respective communications technology (e.g., one of the 802.11x standards, Bluetooth, Ethernet, RS485, cellular data or other communications technology), which can include encryption.

The computing device 904 can provide a graphical user interface (GUI) on the display 916, which includes one or more GUI control elements (e.g., a GUI trigger or button). The computing device 904 sends activation instructions through the link 928 to the control device 910 of the test apparatus device 902 responsive to a user selection or activation of the GUI control element to provide OCT control instructions. Additionally, or alternatively, as described herein, the test apparatus 902 can include a switch, such as one or more switches configured to provide control signals, and the control device 910 can be programmed to control the optical device to perform optical testing (e.g., implement OCT scans and generate OCT test data) in response to the control signals. The switch(es) can be mechanical switches, such as in the form of push buttons (e.g., buttons 200, 202 and/or 204), levers, toggle switches, limit switches, float switches, pressure switches, or the like, which can be activated physically by moving, pressing, releasing, or touching contacts thereof and/or electronic switches activated by semiconductor action without requiring movement of physical contacts. For example, the control device 910 and/or computing device 904 can include an interface configured to receive the control signals from responsive to activation of the buttons (e.g., buttons 200, 202 and/or 204) and activate and/or control respective optical test functions.

In some examples, the test apparatus 902 can provide feedback through the communications link 916 to the instructions (e.g., a client app or other code) running on the computing device 904 to indicate that scanning has been triggered. The control device 910 and/or instructions 926 can be programmed to evaluate at least some of the test data to determine a quality of the test data and provide an output based on the determined quality. The computing device 904 can thus provide visual or audible feedback to the user based on the output representative of the determined quality. Additional sensors and/or other instructions can be configured to provide alerts or other feedback (e.g., visual, audible and/or tactile feedback) to assist users to orient themselves and perform test functions in the absence of a trained technician. For example, the system 900 can be configured to provide other guidance and perform additional functions as set forth in the above incorporated U.S. Patent Pub. No. 2021/0378505 and/or U.S. patent application No. 63/593,665, filed Oct. 27, 2023.

As a further example, an image quality metric can be computed for each optical image. The quality metric can be determined by program code executed by the optical device 908, the control device 910, the computing device 904 and/or the remote system 906. In an example, the control device 910 and/or the computing device 904 is programmed to determine the quality metric as a binary metric that indicates whether or not a quality of the optical image (e.g., a series of scans, such as OCT scans) is acceptable. The OCT image can be generated as a volume scan (e.g., a series of B scans), and the quality analysis is implemented on the batch and, if there are enough images of sufficient quality, the scan as a whole is considered acceptable. The quality of respective scans can be measured based on a total intensity of the OCT image, a signal-to-noise ratio (SNR) of the OCT image and/or based on a quantification of other information contained in image data.

In some examples, the instructions 926 are programmed to provide additional feedback to specify an indication of OCT image quality and/or whether a scan needs to be repeated, such as can be determined by the control device and/or the computing device. The feedback thus can be presented on the display 918 to either indicate that the scan was "successful," that is, of high enough quality for clinical use, or that the scan needs to be retaken. The scan is complete when indicated by a light (e.g., illuminated by the control device) and/or another indication provided on the computing device to specify a fixation point for returning optical device 908. For example, if the user sees a green or other positive confirmation (visual and/or audible) presented by the computing device 904, which indicates a successful scan and the user may leave the device. If the user sees or receives another indication that the scan was incomplete/unsuccessful, which indicates a need to redo the OCT scan, the user is instructed to repeat the process of taking another scan as described herein.

In some examples, the instructions 926 are programmed to provide real-time feedback (e.g., audible and/or visible feedback) to indicate scan quality during testing. The feedback can be provided via a light visible within the eye piece, on the display 918 and/or through a speaker to specify an indication of image quality during the scan process. For example, a light can be red when the image quality is poor and become progressively green as the user correctly orients the user's head relative to the eyepiece. Similar audio tones may also be used to help instruct the user to position their head relative to the eyepiece. In this way, the system 900 can instruct the user when to stop trying to reorient their head during a video/volume scan.

The instructions 926 on the computing device 904 further can be configured to send the acquired OCT data (e.g., one or more image frames) to the remote system 906 responsive to determining that a given scan is "good" or a sufficient number of one or more acquired image frames are acceptable. For example, the OCT system 900 can be programmed to send the remote system a set of one or more image frames determined to be the best frames based on image analysis that is performed on the acquired image frames. In other examples, the entire set of scans can be sent to the remote system 906 automatically or in response to a user input.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processors of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Where the disclosure or claims recite "a,", "an," "a first," or "another" element, or the equivalent thereof, it should be interpreted to include one or more than one such element, neither requiring nor excluding two or more such elements. As used herein, the term "based on" means based at least in part on.

As used herein, the term "and/or" can include any and all combinations of one or more of the associated listed items. As used herein, phrases and/or drawing labels such as "X-Y", "between X and Y" and "between about X and Y" can be interpreted to include X and Y.

It will be understood that when an element is referred to as being "on," "attached" to, "connected" to, "coupled" to, "contacting", "adjacent", etc., another element, it can be directly on, attached to, connected to, coupled to, contacting, or adjacent the other element or intervening elements may also be present. In contrast, when an element is referred to as being, for example, "directly on," "directly attached" to, "directly connected" to, "directly coupled" with, "directly contacting", or "directly adjacent" another element, there are no intervening elements present.

Spatially relative terms, such as "under," "below," "lower," "over," "upper", "proximal", "distal", and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

The invention claimed is:

1. An optical coherence tomography (OCT) test system, comprising:

a housing that contains an OCT device having an eyepiece having an optical axis;

an eyecup assembly coupled to the housing and configured to place one or more respective eyes of a user at an expected position and orientation relative to the eyepiece to enable the user to implement a self-acquired scan, wherein the eyecup assembly has a sidewall extending between proximal and distal end portions and an aperture extending axially through the sidewall, and the distal end portion is coupled to a proximal end of the housing so the aperture is arranged to align with the optical axis, and the eyecup assembly is mechanically biased to provide a depth adjustment for at least the proximal end portion of the eyecup assembly relative to the eyepiece in a direction parallel to the optical axis thereof; and a control device configured to control the OCT device in response to a user input, in which the user input is provided in response to one of (1) an activation of a switch or (2) activation of a graphical user interface element.

* * * * *